United States Patent [19]

Green

[11] Patent Number: 4,821,939

[45] Date of Patent: Apr. 18, 1989

[54] STAPLE CARTRIDGE AND AN ANVILLESS SURGICAL STAPLER

[75] Inventor: David T. Green, Westport, Conn.

[73] Assignee: United States Surgical Corporation, Norwalk, Conn.

[21] Appl. No.: 92,076

[22] Filed: Sep. 2, 1987

[51] Int. Cl.⁴ .............................................. B31B 1/00
[52] U.S. Cl. .............................. 227/19; 227/DIG. 1; 128/334 R
[58] Field of Search ....................... 227/19, 82, 83, 92, 227/DIG. 1; 128/334 R

[56] References Cited

U.S. PATENT DOCUMENTS

| | | | |
|---|---|---|---|
| 2,122,815 | 7/1938 | Hansen | 227/83 |
| 3,315,863 | 4/1967 | O'Dea | 227/DIG. 1 X |
| 3,973,709 | 8/1976 | Akopov et al. | 227/19 |
| 4,206,863 | 6/1980 | Savino | 227/83 |
| 4,232,810 | 11/1980 | Russell | 227/19 |
| 4,375,866 | 3/1983 | Geirsch et al. | 227/19 |

Primary Examiner—Frank T. Yost
Assistant Examiner—James L. Wolfe
Attorney, Agent, or Firm—Kenyon & Kenyon

[57] ABSTRACT

The anvilless surgical stapler includes a pair of stapling assemblies which are mounted on the articulated handles of an applicator. Each stapling assembly includes a mounting block and a staple cartridge which is slidably mounted within the block. Further, each cartridge has a housing with a plurality of openings in which staples are slidably received along with a plurality of pushers. When the stapling assemblies are brought together, one or more ribs in the mounting blocks cause the pushers to fire the staples from the openings of the staple cartridge housings. A pair of deformable lips are also provided at the mouth of each opening for deforming the legs of each staple inwardly toward each other in order to embed into the tissue without penetrating into the tissue. The lips also permit passage of the deformed staples under the biasing force of the pushers.

40 Claims, 7 Drawing Sheets

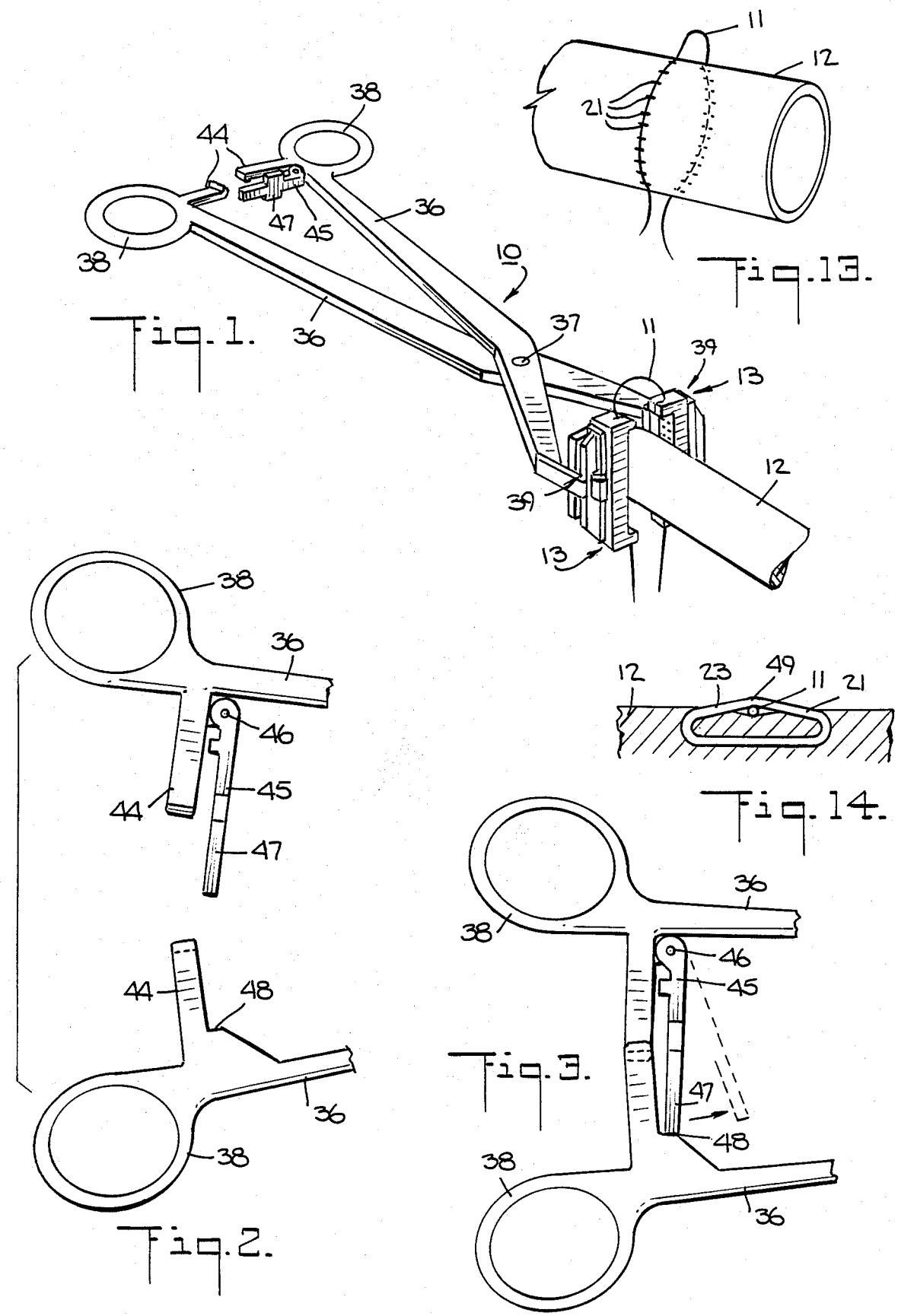

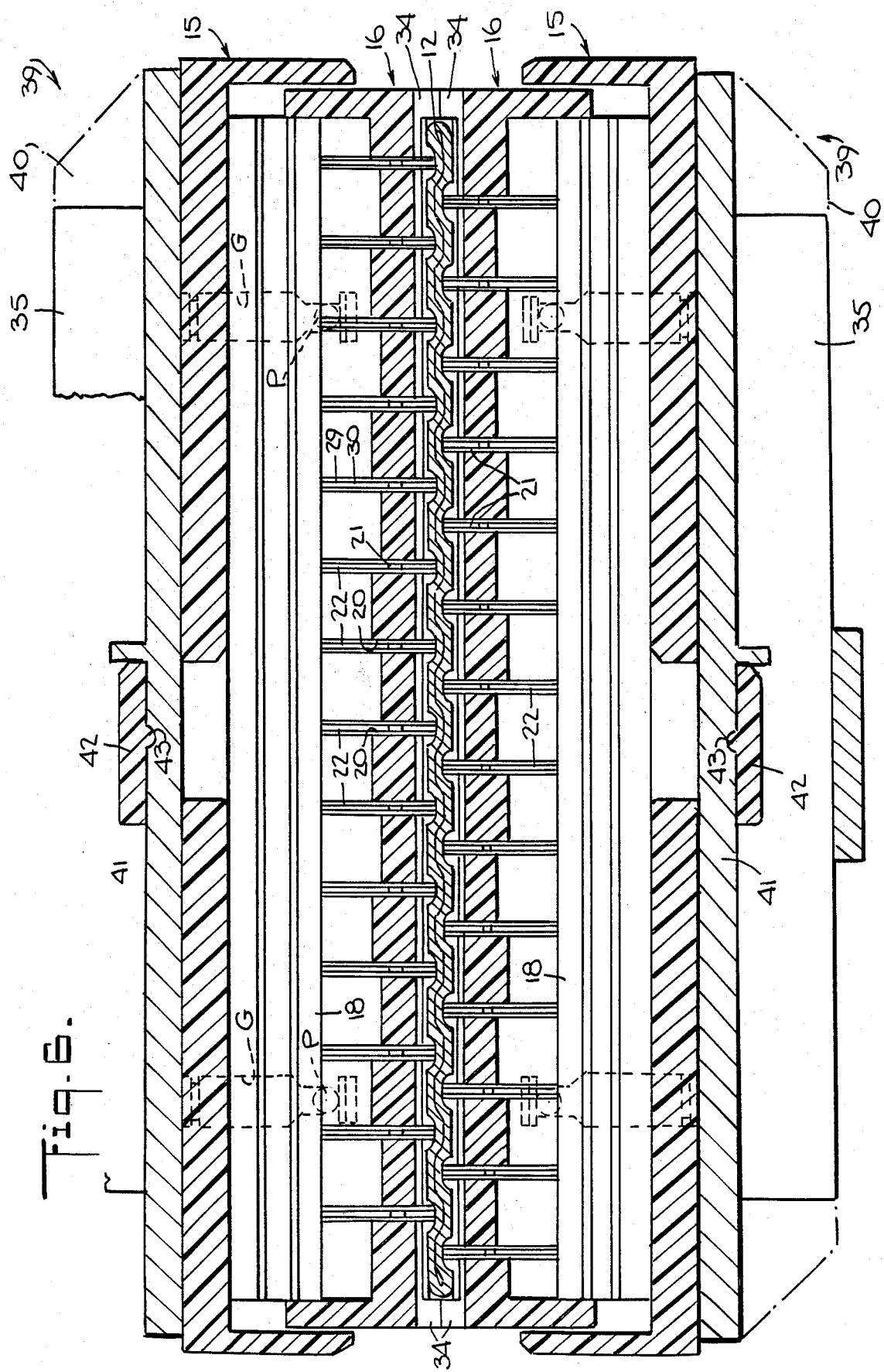

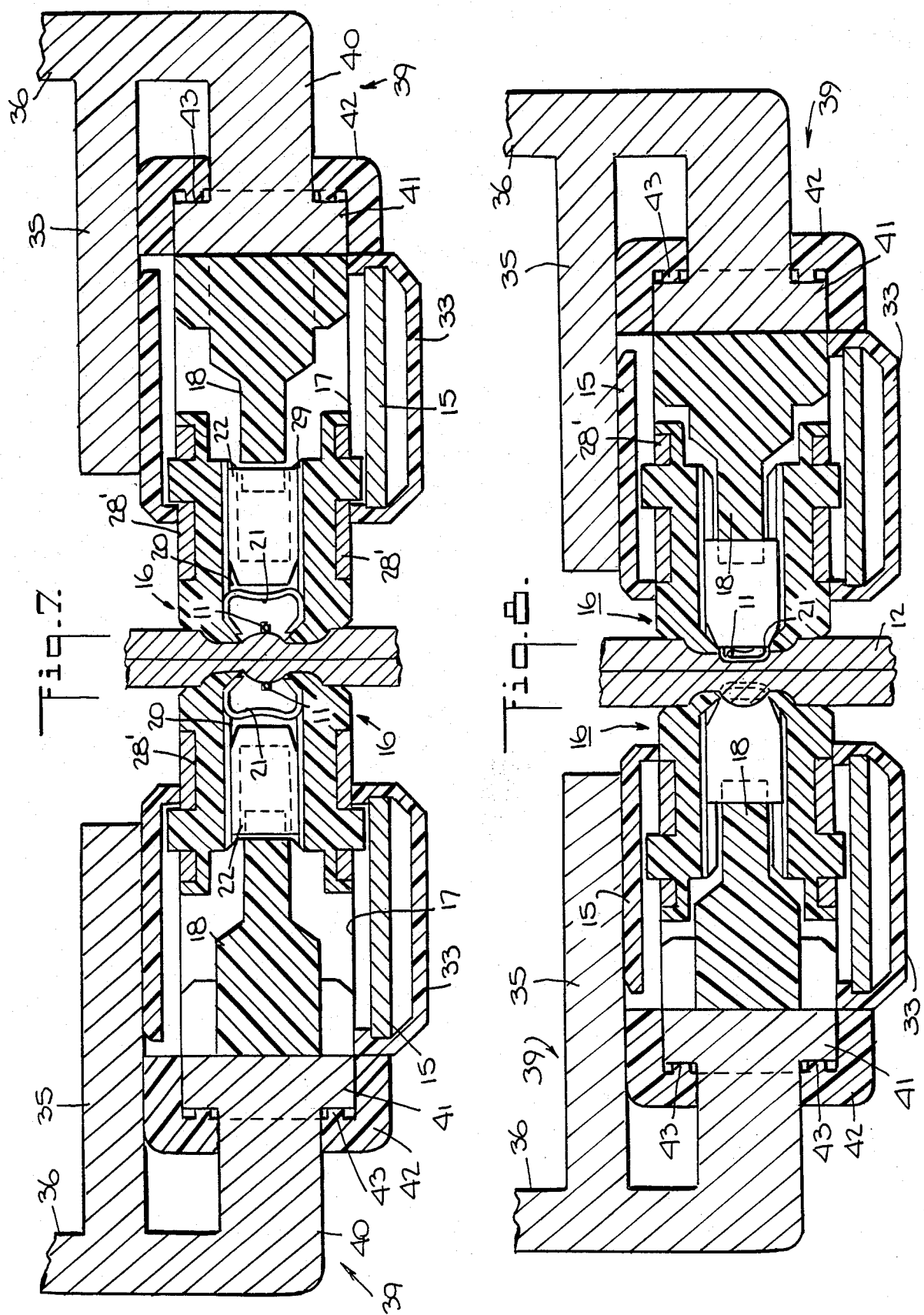

STAPLE CARTRIDGE AND AN ANVILLESS SURGICAL STAPLER

This invention relates to a staple cartridge and, more particularly, to an anvilless surgical stapler and a method of affixing a staple to tissue.

Heretofore, various types of stapling instruments have been known for affixing staples to body tissue. Generally, the staples have been applied by using instruments having an anvil and an ejector mechanism for driving the legs of a staple through the tissue and against the anvil for deforming the legs into a "B" shape or the like. In some cases, the stapling instruments have been used to apply a purse string to the tissue, for example for an end to end anastomosis procedure.

Although various types of instruments have been known for driving the legs of a staple through tissue there are times when it is not desirable or practical to drive the legs of a staple through the body tissue in order to affix a staple. For example it is generally not practical to use a stapling instrument having an anvil for closing an incision in fascia tissue since there is usually limited space for access of an anvil. Further in cases where a purse string is to be applied to a tubular section of tissue the stapling instruments have been rather cumbersome and complex in order to provide an anvil against which the staples can be deformed in order to hold a purse string in place.

Accordingly, it is an object of the invention to provide a relatively simple surgical stapler for applying staples to body tissue without need for an anvil.

It is another object of the invention to provide a relatively simple stapling assembly for a surgical stapler.

It is another object of the invention to be able to affix a staple to body tissue without complete piercing of the tissue by the legs of the staples.

It is another object of the invention to provide a relatively simple instrument for applying a purse string to body tissue.

It is another object of the invention to provide a staple which can be affixed to body tissue without complete piercing of the tissue.

Briefly, the invention provides a one-piece staple which can be affixed to tissue without complete piercing of the tissue. In this regard the staple has a base of a shape to define one of a recess and a projection and a pair of deformable legs which extend from the base with each leg extending angularly inwardly of the base towards the other leg. In addition, each leg has a sharp point at a distal end for penetrating into body tissue. The staple also includes a pair of rounded transition portions each of which extends between the base and one of the legs.

The invention also provides a staple cartridge which includes a housing which may have a plurality of openings a plurality of staples slidably received in the respective openings, a plurality of pushers slidably received in the respective openings of the housing, a first means for simultaneously moving each pusher from a rest position to an actuated position to expel the staples from the openings and a second means on the housing at a mouth of each opening for deforming the legs of each staple inwardly toward each other during movement of each staple through the mouth of each opening in order to penetrate into and engage with the tissue therebetween.

The deforming means of the staple cartridge may be in the form of an inwardly directed pair of lips on the housing at each mouth to define an outlet of less width than the respective opening. In addition, each lip is made to be deformable under a biasing force of the first means in order to permit passage of a deformed staple thereby. Thus, as the staple is being expelled from an opening, the lips first serve to deform the legs of a staple inwardly toward each other so as to penetrate into and grip the tissue. Second the lips are able to move apart to permit passage of the deformed staple under the biasing force.

The staple cartridge may also be constructed so that the housing includes a recess with extends transversely within a plane of the openings in order to receive a purse string therein for expelling within and with the deformed staples. In this regard the staple cartridge is used to attach a purse string to body tissue.

The invention also provides a stapling assembly which is comprised of a mounting block having an internal recess for slidably mounting a staple cartridge therein as well as a centrally disposed rib within the recess for abutting a pusher in response to movement of the housing of a staple cartridge into the recess of the mounting block. This stapling assembly is constructed so that both the block and the cartridge are of elongated rectangular shape with the housing of the staple cartridge containing a plurality of staples. In addition, the mounting block may be provided with a single rib which extends longitudinally of the mounting block in order to abut all of the pushers. Alternatively, the mounting block may include two or more ribs for abutting respective sets of pushers.

The invention also provides an anvilless surgical stapler which is comprised of a pair of stapling assemblies as above and an applicator on which the stapling assemblies are mounted. To this end, the applicator includes a pair of mounting plates disposed in opposed relation to each other with each plate having means for mounting a respective stapling assembly thereon. In addition, the applicator includes a pair of articulated handles connected to the mounting plates for moving the plates toward each other.

Each staple cartridge of a stapling assembly is also provided with a projection at each end for abutting an opposed staple cartridge so as to define a tissue-receiving gap between the cartridges. Thus, the surgical stapler can be initially brought into a clamped position about a tubular section of tissue before firing of the staples. In this respect, the applicator includes a releasable catch mechanism for holding the handles in this tissue-clamping position with the projections of the staple cartridges abutting respective cartridges.

The handles of the applicator are also movable from the tissue-clamping position into a staple firing position upon release of a safety mechanism in order to move each cartridge into a respective housing while expelling the staples through the openings of the respective housings. After firing of the staples, the handles of the applicator can be moved apart so as to complete a stapling operation.

The projections on the staple cartridges may also be arranged to define a groove at each end of the cartridge in order to receive a purse string. In addition, each stapling assembly may be provided with a string retainer on the mounting block thereof for holding a loop of the purse string therein for assembly purposes.

The invention also provides a cartridge assembly which is comprised of a pair of stapling assemblies and a holder which releasably holds the assemblies in somewhat spaced parallel relation. In this respect, the holder is formed of a base plate with a plurality of ribs on one side defining a pair of parallel grooves with each groove receiving a respective retainer of a stapling assembly therein. In addition means are provided for releasably engaging a respective retainer in a respective groove. The holder is also provided with an outwardly extending tab for lifting of the plate from the stapling assemblies after mounting on an applicator.

The invention also provides a method of affixing a staple to tissue wherein a biasing force is applied on the base of a staple to push the legs of the staple into the tissue while simultaneously applying lateral forces against the legs to deform each leg toward the other leg. The forces are applied to the staple with vectors in the same direction, i.e. without any opposed force as from an anvil. In this respect the lateral forces can be applied while pushing the staple through an outlet of less width than the staple.

These and other objects and advantages of the invention will become more apparent from the following detailed description taken in conjunction with the accompanying drawings wherein:

FIG. 1 illustrates a perspective view of an anvilless surgical stapler in accordance with the invention;

FIG. 2 illustrates a partial view of a safety mechanism employed with the handles of the stapler of FIG. 1;

FIG. 3 illustrates a view of the safety mechanism in a tissue-clamping position;

FIG. 6 illustrates a cross sectional view of the mounted stapling assemblies in accordance with the invention;

FIG. 7 illustrates a cross sectional view of the surgical stapler assemblies in a tissue-clamping position;

FIG. 8 illustrates a cross sectional view similar to FIG. 7 of the stapling assemblies in a fired position in accordance with the invention.

FIG. 13 illustrates a tubular section of tissue having a purse string applied thereto by the staple of FIG. 1; and FIG. 14 illustrates a modified stapler constructed in accordance with the invention.

Figure 4:
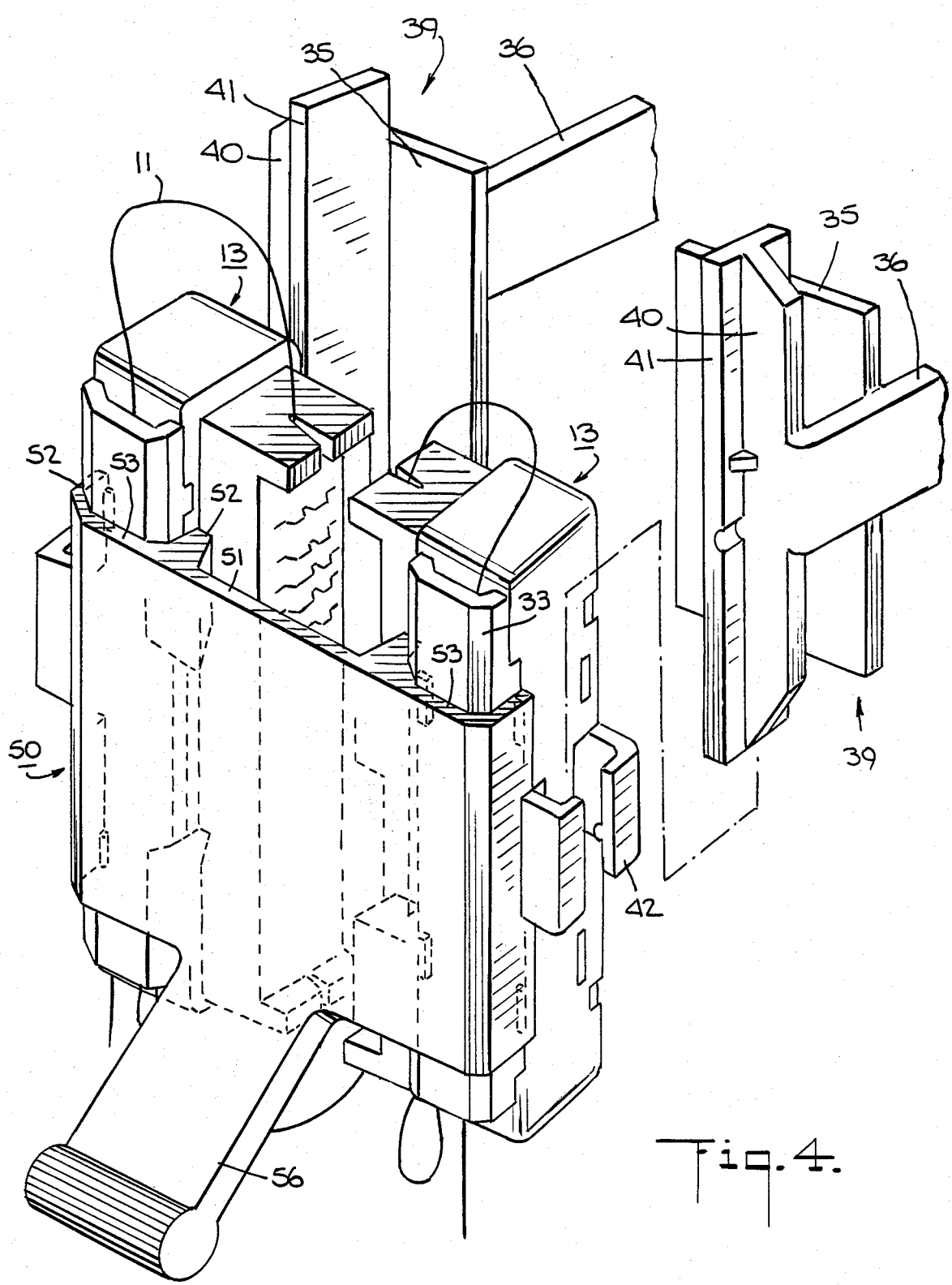
FIG. 4 illustrates an enlarged exploded view of a cartridge assembly for mounting on an applicator in accordance with the invention.

Referring to FIG. 1, the anvilless surgical stapler 10 is used, for example for applying a purse string 11 to a tubular section of tissue 12. In this respect, the term "anvilless" means that there is no opposing anvil or separate member to deform the legs of a staple. As indicated, the stapler 10 includes a pair of stapling assemblies 13 and an applicator 14 constructed in the manner of a forceps.

Figure 5:
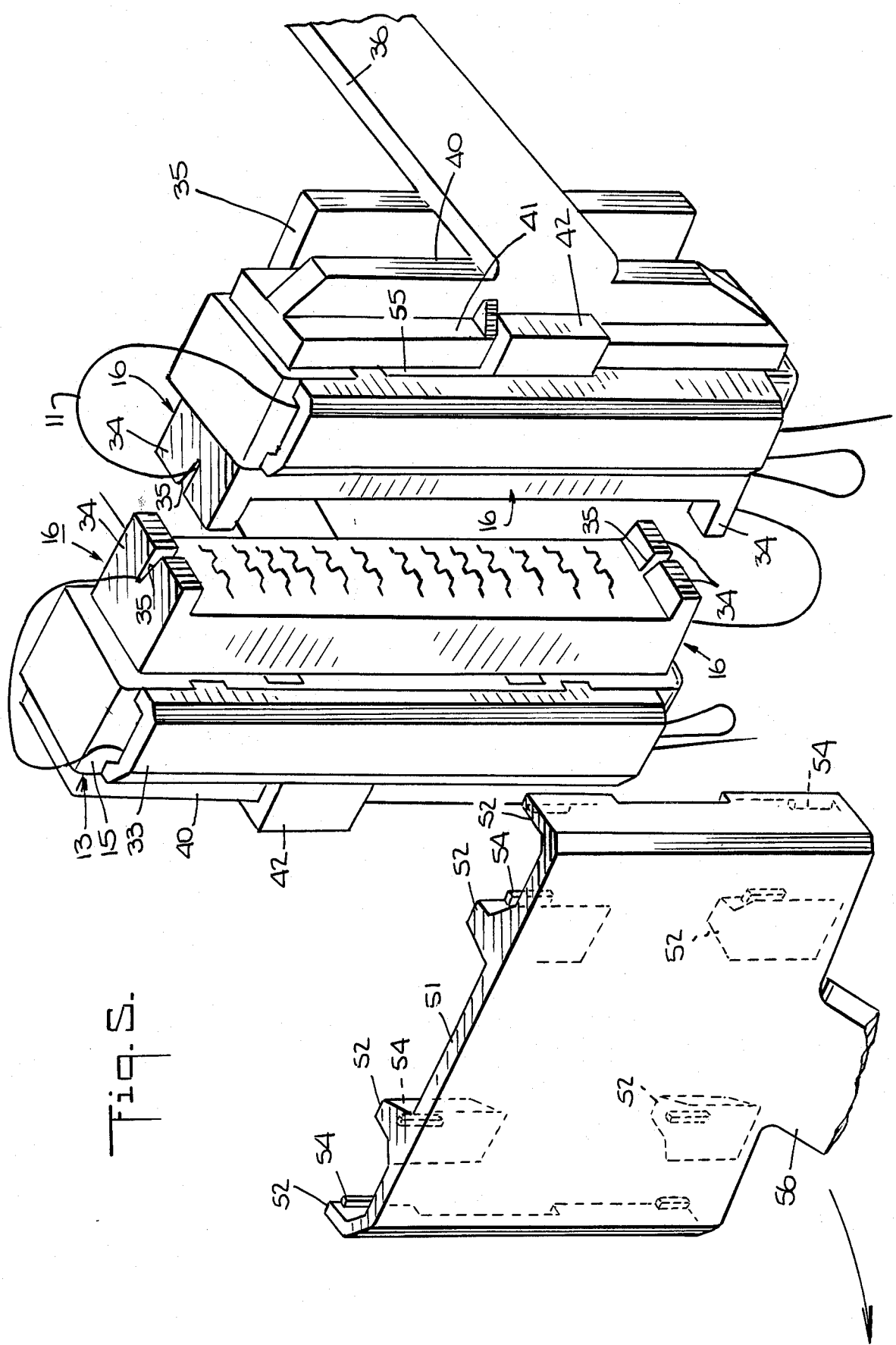
FIG. 5 illustrates a view of a pair of stapling assemblies after mounting on an applicator in accordance with the invention.

Referring to FIGS. 5, 6 and 7, each stapling assembly 13 includes a mounting block 15 and a staple cartridge 16 slidably mounted in the mounting block 15. As indicated in FIG. 5, each of the mounting block 15 and staple cartridge 16 is of elongated rectangular shape.

Referring to FIG. 7, the mounting block 15 includes an internal recess 17 for slidably receiving a staple cartridge 16 as well as a centrally disposed rib 18 within the recess 17. This rib 18 is fixedly secured to the remainder of the block 15. This rib 18 may extend longitudinally of the block 15 or a plurality of discrete ribs (not shown) may be used.

As indicated in FIG. 6, two pins P are provided in each block 15 to provide resistance and to hold the cartridge halves together. Each pin P passes through and is initially at the bottom of a groove G in the block 15 which widens in a direction away from the respective staple cartridge 16.

Referring to FIGS. 6 and 7 each staple cartridge 16 includes a housing 19 having a plurality of longitudinally spaced apart openings 20 in each of which a staple 21 is slidably received. In addition a plurality of pushers 22 are slidably mounted within the housing 19 with each pusher 22 being aligned with an opening 20 and a staple 21 therein as well as in alignment with a rib 18 for abutting there against.

Figure 9:
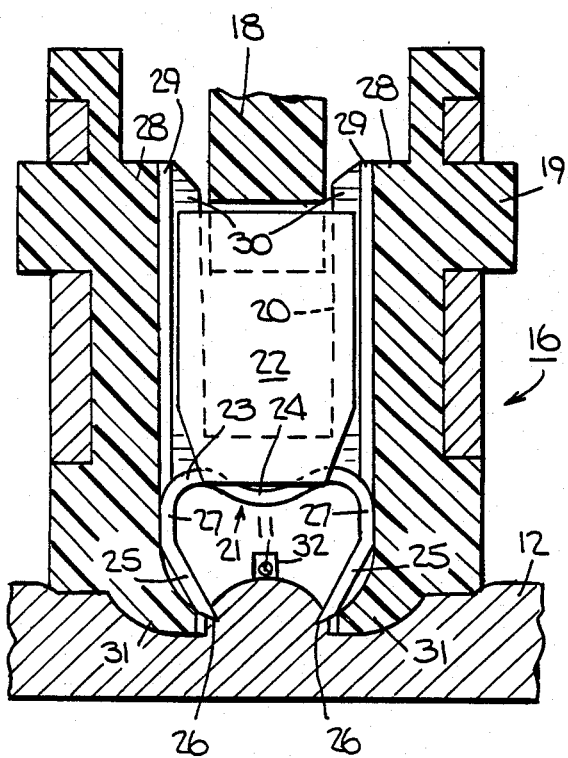
FIG. 9 illustrates a partial view of a stapling assembly in an initial deformation position.

Referring to FIG. 9, each staple 21 is of one-piece construction having a base 23 of undulating shape to define a recess 24 and a pair of deformable legs 25 which extend from the base 23. As indicated, each leg 25 extends angularly inwardly of the base 23 towards the other leg 25 and has a sharp point 26 at the distal end.

Each staple 21 also includes a pair of rounded transition portions 27 each of which extends between the base 23 and a leg 25. Further, each leg 25 is disposed on a rectilinear axis with the sharp point defined for example by an included angle of 35°. The staple 21 is made of any suitable cross section such as a circular cross-section as well as of any suitable material for the purposes intended such as stainless steel and absorbable materials.

Referring to FIG. 9 the housing 19 has a pair of opposed walls 28 defining each internal opening 20. In addition each wall 28 is provided on the outside with a stiffener plate 28' and has a first slot 29 extending longitudinally of the opening 20 in order to slidingly receive one side of a staple 21, that is, a rounded transition portion 27. In addition a second slot 30 of greater width than the slot 29 extends coaxially of the slot 29 in order to slidably receive one side of a pusher 22.

As indicated in FIG. 9, the width of a staple 21 is greater than the width of a pusher 22. Further the lower surface of each pusher 22 is provided with a surface complementary to the undulating base 23 of a staple 21 so as to have a projection (not shown) seated in the recess 24 of the staple 21. This arrangement serves to center the staple 21 within the opening 20 while also ensuring uniform motion of a staple 21 out of the opening 20.

A means for deforming the legs 25 of a staple 21 at the mouth of each opening 20 is constituted by a pair of inwardly directed lips 31. As indicated, each lip 31 is disposed at one end of the staple receiving slot 29 in a wall 28. Further, the lips 31 are spaced apart to define an outlet of less width than the opening 20 and less width than a staple 21. In this respect, the housing 19 is made of a material sufficient to permit deformation of the legs 25 of a staple 21 while at the same time being deformable to spread apart to permit passage of a deformed staple 21 under a biasing force on the respective pushers 11. Each lip 31 may also be of material resilient enough to permit the passage of a deformed staple while still capable of returning to its previous position and form. Such resiliency is required if successive staples are fired as, for example, in a skin stapler. Additionally lips 31 may have an articulation means for achieving such resiliency.

As indicated in FIG. 9 the tip of each staple leg 25 is angled such that the heel (i.e. rear) of the angled tip slides within a slot 29 so that the sharp tip does not dig into the lip 31 during firing. In this respect, the slot 29 is curved within the lip 31.

Referring to FIGS. 7 and 8, the ribs 18 constitute a means for moving the pushers 22 from a rest position in the respective housings 19, as indicated in FIG. 7, to an actuated position, as indicated in FIG. 8, adjacent the outlet of each opening 20. In this respect, a suitable means such as a bar may be connected to one or more pushers 22 in order to move the pushers simultaneously.

Figures 11, 12:
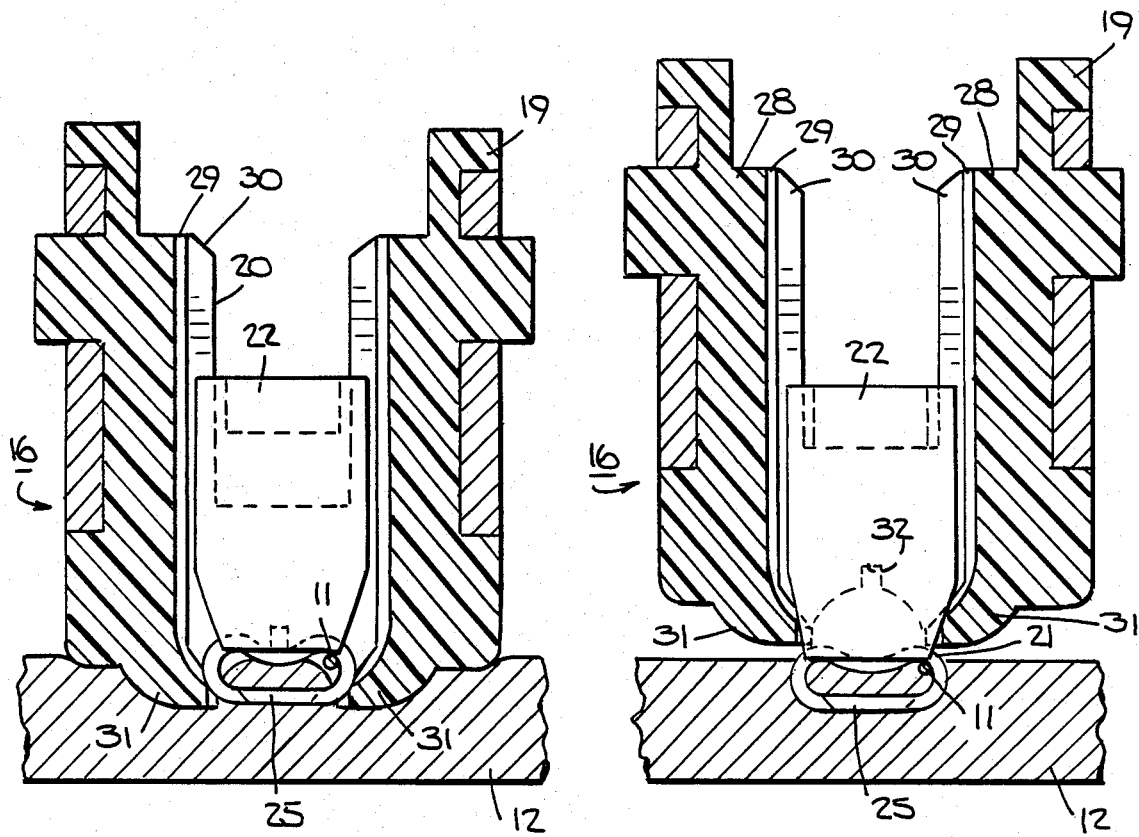
FIG. 11 illustrates a view similar to FIGS. 9 and 10 of a deformed staple in accordance with the invention.
FIG. 12 illustrates a view similar to FIGS. 9, 10 and with a deformed staple expelled from a stapling assembly in accordance with the invention.

As indicated in FIGS. 9 and 12, each housing 19 includes a recess 32 which extends along the housing 19 transversely of and across the respective openings 20 to receive a purse string 11.

Referring to FIG. 6 the openings 20 and respective staples 21 of each cartridge 16 are offset longitudinally of the openings 20 and staples 21 of the opposed cartridge 16. This allows the clamped tissue 12 to protrude into the openings 20 and also inhibits the staples 21 from penetrating both sides of the tissue 12.

Referring to FIG. 5 each stapling assembly 13 includes a retainer 33 which is mounted in fixed relation on a mounting block 15. As indicated each retainer 33 defines an elongated space within which a loop of the string 11 may be retained.

As also indicated in FIG. 5, each cartridge 16 has a projection extending from each end of the housing 19 for abutting an opposed cartridge 16 in order to define tissue-receiving gap as indicated in FIG. 6 between the cartridges 16. This gap is such as to avoid crushing of the tissue. Further, each projection 34 can be provided with a recess 35 to receive a length of the purse string 11 therein.

The projections 34 also serve to transfer the forces necessary to fire the stapler. Alternatively each staple cartridge may have a single projection at each end which is about half the width of a cartridge housing 19 so as to abut an aligned cartridge housing 19 while aligning with a similar projection of the opposed cartridge. In this case, the purse string would extend between the two projections at each end of the cartridges.

Referring to FIG. 1, the applicator 14 includes a pair of mounting plates 35 which are disposed in opposed relation to each other and a pair of articulated handles 36 which are connected to the mounting plates 35 for moving the plates 35 towards each other. As indicated, the handles 36 are pivotally connected to each other about a pivot pin 37. Also, each handle 36 includes a finger gripping portion 38 at a proximal end. A spring (not shown) may also be provided to bias the handles 36 apart.

Referring to FIG. 4, each mounting plate 35 has means 39 for mounting a respective stapling assembly 13 thereon. As indicated, each means 39 includes a bracket 40 integral with a plate 35 from which a mounting leg 41 extends in spaced relation to the mounting plate 35. In addition each stapling assembly 13 is provided with a sleeve-like connector 42 which releasably receives a mounting leg 41. A suitable detent (not shown) may be provided in the sleeve connector 42 to be releasably engaged in a groove 43 of the mounting leg 41.

In order to mount a stapling assembly 13 in place the sleeve connector 42 is slid over mounting leg 43 until the detent (not shown) catches in the groove 43 of the mounting leg 41.

Referring to FIG. 1 the applicator 10 includes a catch mechanism 44 which serves to approximate a predetermined clamping position of the applicator 10. This mechanism 44 is disposed on the handles 36 at the proximal ends and is of generally known construction and need not be further described. In addition, a safety mechanism 45 is provided at the proximal end for stopping the handles 36 in a tissue-clamping position (as indicated in FIG. 6) with the projections 34 abutting a respective cartridge 16. As indicated in FIGS. 1 and 2 the safety mechanism 45 is in the form of a lever which is pivotally mounted about a pin 46 on the catch mechanism 44 and includes a lateral tab 47 which is sized to permit pivoting of the lever 45 by a thumb of a surgeon. As indicated in FIG. 3 when in the tissue-clamping position, the lever 45 abuts against an abutment surface 48 on the opposite handle 36 while the catch mechanism 44 holds the handles 36 in place.

Referring to FIG. 4, a holder 50 is provided to releasably hold a pair of stapling assemblies 13 in order to form a cartridge assembly. As indicated the holder 50 is formed of a base plate 51 with a plurality of ribs 52 on one side forming a pair of parallel spaced apart grooves 53 for receiving a retainer of each stapling assembly 13. In addition means are provided for releasably engaging each retainer 33 in a respective groove 53. For example, the means may be in the form of small projections 54 which fit into small spaces 55 between each retainer 33 and a mounting block 15 of a stapling assembly 13 (see FIG. 5). As indicated the grooves 53 may be discontinuous that is the internal ribs 52 need not extend the length of the plate 51. Alternatively, the holder 50 may grip the assemblies 13 at the ends rather than the sides as shown.

The holder 50 is also provided with an outwardly extending tab 56 at one end of the plate 51. This tab 56 serves to lift the plate 51 from the stapling assemblies 13 after mounting of the assemblies 13 on the mounting plates 35 on the handles 36 of the applicator 14. Alternatively, instead of using a tab 56, a pair of finger engaging recesses may be provided on opposite ends of the plate 51, for example on the lower end of the plate 51 as viewed in FIG. 4.

In use, the stapler 10 may be provided with the stapling assemblies 13 in place. If not, a cartridge assembly as indicated in FIG. 4 may be brought to the mounting plates 35 with the handles 36 in an opened rest position. At this time, the stapling assemblies 13 can be slid onto the respective mounting legs 41 and snap-fitted in place as indicated in FIG. 5. Thereafter, the holder 50 can be removed, for example, by a slight tilting up of the plate 51 from the retainers 33.

Thereafter, the stapler 10 can be brought into position about a tubular section of tissue 12 as indicated in FIG. 1. Next, the handles 36 can be brought into a tissue-clamping position with the catch mechanism 44 engaged and the safety mechanism lever 45 in abutment with the surface 48 as indicated in FIG. 3. At this time the projections 34 of the staple cartridges 16 are in abutment with the tissue 12 in a collapsed condition as indicated in FIGS. 6 and 7. At this point, the staples 21 have not been engaged by the pushers 22. Further the stapler 10 can be opened and re-positioned by moving the handles 6 apart in this position without projection of the staplers 21 from the cartridges 16.

Next the safety mechanism 45 is released into the dotted line position of FIG. 3 and the handles 36 are brought further together in order to fire the staples 21 from the cartridges 16 as indicated in FIG. 8

As indicated in FIGS. 9 to 12, during firing each staple 21 is deformed into a layer of tissue 12 without piercing through the tissue layer. Initially as indicated in FIG. 9 the deformable legs 25 of the staple abut against the deformable lips 31 with the sharp ends 26 projecting into the mouth of a respective opening 20. The layer of tissue 12 deforms about the lips 31 so as to enter slightly into the mouth of each opening 20 and may be slightly penetrated by the sharp tips of the staples 21.

As the handles 36 are brought together, the mounting blocks 15 of the staple assemblies 13 move toward each other as indicated in FIG. 8. However, the housings 19 of the respective staple cartridges 16 remain in place. That is, each mounting block 15 moves relative to the stapled cartridge 16 therein. At this time, the rib 18 of each mounting block 15 abuts the pushers 22, or a bar common to the pushers 22 so as to drive the pushers 22 towards the mouth of each opening 20 as indicated in FIG. 10.

Figure 10:
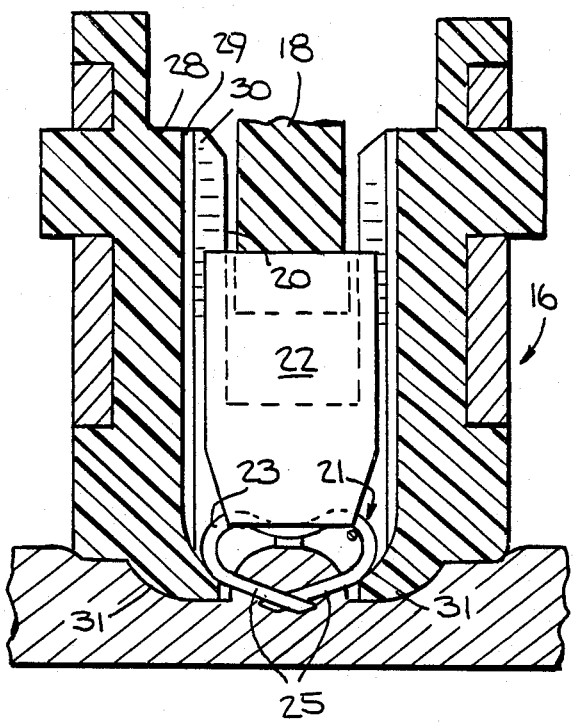
FIG. 10 illustrates a view similar to FIG. 9 during further deformation of a staple in accordance with the invention.

Initially, as indicated in FIG. 10, each staple 21 is pushed under a biasing force applied to the base 23 while lateral forces are simultaneously applied against the legs 25 by the lips 31 so that the legs 25 begin to deform and move towards each other while penetrating into the layer of tissue 12.

As indicated in FIG. 11, near the end of each stroke of a pusher 22 the legs 25 of a staple have been substantially deformed so as to be in crossing relation to each other. In this position, the staples will not readily pull out from the layer of tissue 12. At the same time, the string 11 which has been positioned in the longitudinal recess 32 of a cartridge housing 19 is pushed out of the recess 32 to one or the other side of the deformed staple 21.

As indicated in FIG. 11, the deformed staple 21 is of greater width than the mouth of the opening 20 so as to engage against the deformable lips 31.

Referring to FIG. 12, as the stroke of a pusher 22 is completed, the biasing force on the pusher 22 is sufficient to push the deformed staple 21 through the outlet of the mouth of the opening 20 past the lips 31 while deforming the lips 31 sufficiently to permit passage. The amount of deformation of the lips 31 is sufficient to permit passage of the deformed staple 21 while at the same time being insufficient to overly compress the layer of tissue 12.

Once the stapler has been fired, the purse string 11 is automatically pulled from the retainers 33 as the stapler 10 is removed from the area.

Of note the staples 21 only penetrate the tissue 12 to a depth sufficient to remain embedded as the string 11 is drawn and the tissue 12 bunched together in a subsequent operation. In this respect, a purse string normally ties the end of an opening in the hollow tissue such as an intestine stomach and the like.

After firing of the staples 21 the handles 36 can be held in place by the catch mechanism 44. Alternatively the catch mechanism 44 can be released so that the handles 36 are biased apart by the spring (not shown) therebetween.

As indicated in FIG. 13 after removal of the stapler 10, the purse string 11 is held in place by the various staples which have been affixed to the tissue 12. Of note, depending upon the shifting of the string 11 to one side or the other within a staple 21, the string 11 may take a somewhat uneven path about the tissue 12.

Referring to FIG. 14, in order to centralize the string 11, the base 23 of each staple 21 may be provided with a projection for reception in a suitable mating recess in the bottom surface of a pusher (not shown). In this case, as each staple is being expelled, the purse string 11 tends to be centered within each deformed staple 21, Various modifications may be made within the stapler. For example, the mounting arrangement of a staple cartridge on the applicator may be modified. For example, the mounting block of each cartridge may have a pair of tabs which can be slidably received in a mounting head on the end of a handle 36.

Further, each staple may be made with a flat base and/or with legs that are angled toward each other and are sized so as not to cross each other When deformed depending on the use of the staple, for example, for closing an incision rather than for application of a purse string.

The invention thus provides a stapler which can be utilized for applying a purse string to body tissue. However the stapler may also be used as a skin or fascia stapler in which case use may be made of only one staple assembly. Where only one staple assembly is used, the staples may be fed and deformed singly. Also, the stapler may be constructed and adapted for use in eye surgery for the closing of incisions.

The invention also provides a method of affixing a staple to tissue wherein a biasing force is applied to the base of a staple to push the legs of the staple into the tissue while simultaneously applying lateral forces against the legs to deform each leg toward the other leg. Such forces are applied to the staple without any opposed force as from an opposed anvil.

What is claimed is:

1. A staple cartridge comprising
   a housing having a pair of opposed walls defining an internal opening therebetween, each said wall having a first slot extending longitudinally of said opening to receive one side of a staple therein, a second slot of greater width coaxially of said first slot and an inwardly directed lip at one end of said first slot to define an outlet of less width than said opening and a staple in said opening;
   a pusher slidingly received in said second slot of each wall and extending across and between said walls for expelling a staple disposed in said slots of said walls through said outlet; and
   means for moving said pusher from a rest position in said housing to an actuated position adjacent said outlet.

2. A staple cartridge as set forth in claim 1 wherein said housing has a plurality of said openings therein for receiving a plurality of staples and a plurality of pushers for expelling the staples, said means being connected to said pushers to move said pushers simultaneously.

3. A staple cartridge as set forth in claim 1 wherein each lip is of material sufficient to permit deformation of a staple therein under a biasing force of said means and said pusher.

4. A staple cartridge as set forth in claim 3 wherein each lip is deformable under a biasing force of said means to move away from the other lip to permit passage of a deformed staple thereby.

5. A staple cartridge as set forth on claim 1 wherein said housing includes a recess for receiving a purse string therein, said recess extending transversely of and across said opening.

6. A staple cartridge for tissue comprising
   a housing having a plurality of openings therein;
   a plurality of staples, each staple being slidably received in a respective opening and including a base and a pair of legs extending perpendicularly from said base each said leg being of a width equal to the width of said base;
   a plurality of pushers, each said pusher being slidably received in a respective opening of said housing;
   first means in said housing for simultaneously moving each pusher from a rest position thereof to an actuated position to expel said staples from said openings; and
   second means on said housing at a mouth of each opening for deforming said legs of each staple inwardly toward each other during movement of each staple through said mouth of each respective opening to penetrate into and engage with tissue therebetween.

7. A staple cartridge as set forth in claim 6 wherein said first means includes a pusher bar connected in common to said pushers.

8. A staple cartridge as set forth in claim 6 wherein each pusher has a protuberance and each staple has a recess in said base thereof receiving said protuberance.

9. An anvilless stapler comprising
   a cartridge having a plurality of openings, a plurality of staples slidably received in said openings and including a base and a pair of legs extending from said base, and a plurality of pushers slidably received in said openings to abut a respective base of said staples;
   first means for simultaneously moving each pusher from a rest position to an actuated position to expel said staples from said openings; and
   a deformable second means on said housing at a mouth of each opening for deforming said legs of each staple inwardly toward each other during movement of each staple through said mouth of each respective opening to penetrate into and engage with tissue therebetween.

10. An anvilless stapler as set forth in claim 9 wherein said second means includes an inwardly directed pair of lips on said housing at each mouth to define an outlet of less width than said respective opening.

11. An anvilless stapler as set forth in claim 10 wherein each lip is deformable under a biasing force of said first means to permit passage of a deformed staple thereby.

12. An anvilless stapler as set forth in claim 10 wherein said housing includes a recess extending transversely within a plane of said openings to receive a purse string therein for expelling with and within the deformed staples.

13. A stapling assembly for an anvilless surgical stapler comprising
    a mounting block having an internal recess and a centrally disposed rib within said recess; and
    a staple cartridge slidably mounted within said recess of said block, said cartridge including a housing having at least one opening, a staple slidably received in said opening and including a base and a pair of legs, a pusher slidably received in said housing between and in alignment with said central rib and said staple, means at a mouth of said opening for deforming said legs of said staple inwardly towards each other during movement through said mouth in response to movement of said housing into said recess of said mounting block.

14. A stapling assembly as set forth in claim 13 wherein each of said block and said cartridge is of elongated rectangular shape.

15. A stapling assembly as set forth in claim 14 which includes a plurality of said openings in said housing and a corresponding plurality of said staples and said deforming means.

16. A stapling assembly as set forth in claim 15 wherein said mounting block includes at least two of said ribs.

17. A stapling assembly as set forth in claim 15 wherein said rib extends longitudinally of said mounting block.

18. An anvilless surgical stapler comprising
    a pair of stapling assemblies, each said assembly including a mounting block having an internal recess and a centrally disposed rib within said recess; and
    a staple cartridge slidably mounted within said recess of said block, said cartridge including a housing having at least one opening, a staple slidably received in said opening and including a base and a pair of legs, a pusher slidably received in said housing between and in alignment with said central rib and said staple, means at a mouth of said opening for deforming said legs of said staple inwardly towards each other during movement through said mouth in response to movement of said housing into said recess for mounting block; and
    an applicator including a pair of mounting plates disposed in opposed relation to each other, each plate having means for mounting a respective stapling assembly thereon and a pair of articulated handles connected to said mounting plates for moving said plates toward each other.

19. An anvilless surgical stapler as set forth in claim 18 wherein each staple cartridge has a projection extending from each end of said housing for abutting an opposed staple cartridge to define a tissue-receiving gap between said cartridges and said applicator includes a releasable catch mechanism for holding said handles in a tissue clamping position with said projections abutting a respective cartridge.

20. An anvilless surgical stapler as set forth in claim 19 which includes a plurality of said openings in each housing and a corresponding plurality of said staples and said deforming means.

21. An anvilless surgical stapler as set forth in claim 20 wherein said handles are movable from said tissue clamping position into a staple firing position upon release of said catch mechanism to move each cartridge into a respective housing while expelling said staples through said openings of said housings.

22. An anvilless surgical stapler as set forth in claim 20 wherein said projections define a groove at each end of a respective cartridge to receive a purse string thereon.

23. An anvilless surgical stapler as set forth in claim 22 wherein each housing includes a recess extending transversely of said openings therein to receive a purse string therein.

24. An anvilless surgical stapler as set forth in claim 22 wherein each stapling assembly includes a string retainer on said mounting block thereof for holding a loop of a purse string therein.

25. An anvilless surgical stapler comprising
a pair of stapling assemblies, each assembly including a mounting block, a staple cartridge slidably mounted in said block and including a housing having a plurality of openings, a plurality of staples slidably received in said openings, each said staple having a pair of legs, a plurality of pushers slidably received in said housing in alignment with said pushers and means at a mouth of each opening for deforming said legs of each respective staple inwardly towards each other during movement through said mouth; and
an applicator including a pair of mounting plates disposed in opposed relation to each other, each plate having means for mounting a respective stapling assembly thereon and a pair of articulated handles connected to said mounting plates for moving said plates toward each other.

26. An anvilless surgical stapler as set forth in claim 25 wherein each staple cartridge has a projection extending from each end of said housing for abutting an opposed staple cartridge to define a tissue-receiving gap between said cartridges and said applicator includes a releasable catch mechanism for holding said handles in a tissue clamping position with said projections abutting a respective cartridge.

27. An anvilless surgical stapler as set forth in claim 26 wherein said handles are movable from said tissue-clamping position into a staple firing position upon release of said catch mechanism to move each cartridge into a respective housing while expelling said staples through said openings of said housings.

28. An anvilless surgical stapler as set forth in claim 25 wherein each stapling assembly includes means in said housing thereof for simultaneously abutting said pushers during movement of said housing into said mounting block thereof o simultaneously expel said staples therefrom.

29. A cartridge assembly comprising
a pair of stapling assemblies, each assembly including a mounting block a staple cartridge slidably mounted in said block and having a plurality of staples therein for stapling into tissue and a retainer mounting on said mounting block; and
a holder releasably holding said assemblies in spaced parallel grooves, each said groove receiving a respective retainer therein and means for releasably engaging a respective retainer in a respective groove.

30. A cartridge assembly as set forth in claim 29 wherein said holder includes a base plate, a plurality of ribs on said plate defining said grooves and an outwardly extending tab integral with said plate for lifting said plate from said stapling assemblies after mounting of said assemblies on an applicator.

31. A method of affixing a staple having a base and a pair of legs extending therefrom to tissue, said method comprising the steps of
positioning a purse string transversely between the staple legs;
applying a biasing force on the base of the staple to push the legs into the tissue; and
simultaneously applying lateral forces against the legs to deform each leg toward the other leg.

32. In a stapler for tissue, the combination comprising
a housing having a pair of opposed walls defining an opening therebetween;
a staple mounted within said opening in said housing and having a base extending across said opening and a pair of deformable legs extending from said base;
a pusher slidably mounted in said housing in alignment with said opening and said staple therein; and
means at a mouth of said opening of said housing for deforming said legs of said staple inwardly toward each other within said opening and into tissue thereat prior to movement of said staple through said mouth, said means being deformable and defining an outlet of less width than said opening and less width than said base.

33. The combination as set forth in claim 32 wherein each said wall has a first slot slidably receiving one side of said staple and a second coaxial slot slidably receiving one side of said pusher.

34. The combination as set forth in claim 32 wherein said means includes a lip extending from each wall towards the opposite wall to apply a lateral force against a respective leg for deforming said leg.

35. The combination as set forth in claim 34 wherein said lips are resiliently deformable to permit passage of the deformed staple thereby.

36. The combination as set forth in claim 32 wherein said pusher has a protuberance and said staple has a recess in said base receiving said protuberance.

37. A staple cartridge for tissue comprising
a housing having a plurality of openings therein;
a plurality of staples, each staple being slidably received in a respective opening and including a base and a pair of legs extending from said base;
a plurality of pushers, each said pusher being slidably received in a respective opening of said housing;
means in said housing for simultaneously moving each pusher from a rest position thereof to an actuated position to expel said staples from said openings; and
means including an inwardly directed pair of lips on said housing at a mouth of each opening to define an outlet of less width than said respective opening for deforming said legs of each staple inwardly toward each other during movement of each staple through said mouth of each respective opening to penetrate into and engage with tissue therebetween.

38. A staple cartridge as set forth in claim 37 wherein each lip is deformable under a biasing force of said first means to permit passage of a deformed staple thereby.

39. A staple cartridge for tissue comprising
a housing having a plurality of openings therein and a recess extending transversely within a plane of said openings to receive a purse therein;
a plurality of staples, each staple being slidably received in a respective opening and including a base and a pair of legs extending from said base;
a plurality of pushers, each said pusher being slidably received in a respective opening of said housing;
first means in said housing for simultaneously moving each pusher from a rest position thereof to an actuated position to expel said staples with the purse string therein from said openings; and second means on said housing at a mouth of each opening for deforming said legs of each staple inwardly toward each other during movement of each staple through said mouth of each respective opening to penetrate into and engage with tissue therebetween while securing the purse string to the tissue.

40. A method of affixing a stapling having a base and a pair of legs extending therefrom to tissue, said method comprising the steps of
   applying a biasing force on the base of the staple to push the legs into the tissue; and
   pushing the staple through a deformable outlet of less width than the staple to simultaneously apply lateral forces against the legs to deform each leg toward the other leg.

* * * * *

UNITED STATES PATENT AND TRADEMARK OFFICE
CERTIFICATE OF CORRECTION

PATENT NO. : 4,821,939

DATED : April 18, 1989

INVENTOR(S) : David T. Green

It is certified that error appears in the above-identified patent and that said Letters Patent is hereby corrected as shown below:

```
Column 3,  line 54 "9, 10 and" should be -9, 10 and 11-
Column 4,  line 8  "Well" should be -well-
Column 5,  line 39 "define" should be -define a-
Column 5,  line 66 "Which" should be -which-
Column 7,  line 5  "6" should be -36-
Column 8,  line 24 "When" should be -when-
Column 9,  line 14 "base each" should be -base, each-
Column 11, line 47 "block a" should be -block, a-
Column 14, line 1  "stapling" should be -staple-
```

Signed and Sealed this

Twentieth Day of February, 1990

*Attest:*

JEFFREY M. SAMUELS

*Attesting Officer*   *Acting Commissioner of Patents and Trademarks*